United States Patent [19]

Rickerd

[11] Patent Number: 5,322,509
[45] Date of Patent: Jun. 21, 1994

[54] CARDIAC CATHETER

[75] Inventor: Claude L. Rickerd, Des Moines, Iowa

[73] Assignee: Iowa Methodist Medical Center, Des Moines, Iowa

[21] Appl. No.: 1,578

[22] Filed: Jan. 6, 1993

[51] Int. Cl.$^5$ .................... A61M 25/00; A61M 31/00
[52] U.S. Cl. ...................... 604/53; 604/280; 128/658
[58] Field of Search ............ 604/204, 280, 282, 50–53; 128/656, 658

[56] References Cited

U.S. PATENT DOCUMENTS

| | | | |
|---|---|---|---|
| 4,117,836 | 10/1978 | Erikson. | |
| 4,169,464 | 10/1979 | Obrez | 128/657 |
| 4,563,181 | 1/1986 | Wijayarathna et al. | 604/280 |
| 4,784,639 | 11/1985 | Patel | 604/53 |
| 4,790,831 | 12/1988 | Skribiski | 604/282 |
| 4,867,174 | 9/1989 | Skribiski | 128/772 |
| 4,886,506 | 12/1989 | Lovgren et al. | 604/280 |
| 4,898,591 | 2/1990 | Jang et al. | 604/282 |
| 4,935,017 | 6/1990 | Sylvanowicz | 604/280 |
| 5,016,640 | 1/1991 | Ruiz | 128/658 |
| 5,045,072 | 9/1991 | Castillo et al. | 604/280 |
| 5,195,990 | 3/1993 | Weldon | 604/281 |
| 5,203,776 | 4/1993 | Durfee | 604/264 |
| 5,231,994 | 8/1993 | Harmjanz | 128/772 |

FOREIGN PATENT DOCUMENTS 2529083 3/1981 France.

OTHER PUBLICATIONS 3 pages discussing Cardiac Catheterization (date & author unknown).
pp. 174–180 from Cardiac Catheterization & Angiography (date and author unknown).
SCIMED Life Systems, Inc., The New 7F Triguide Guiding Catheter (4 pages), 1991.
Bard USCI Division, Dr. Richard K. Myler, Dura-Guide Guiding Catheter, also Dr. Charles A. Simonton, III, (date unknown) 4 pages.

Primary Examiner—John D. Yasko
Assistant Examiner—Adam J. Cermak
Attorney, Agent, or Firm—Zarley, McKee, Thomte, Voorhees & Sease

[57] ABSTRACT

A catheter for cardiac procedures includes a generally C-shaped distal end which roughly conforms to the shape of an aortic arch. The catheter is made of a flexible material and includes a distal portion having a proximal section connected to an intermediate section at approximately 135 degrees. The distal most section attached to the intermediate section is generally perpendicular to the intermediate section and consists of a double or reverse curve. The structure allows the catheter to be utilized to enter either left or right ostia without catheter exchange by rotation of the catheter around its axis.

19 Claims, 1 Drawing Sheet

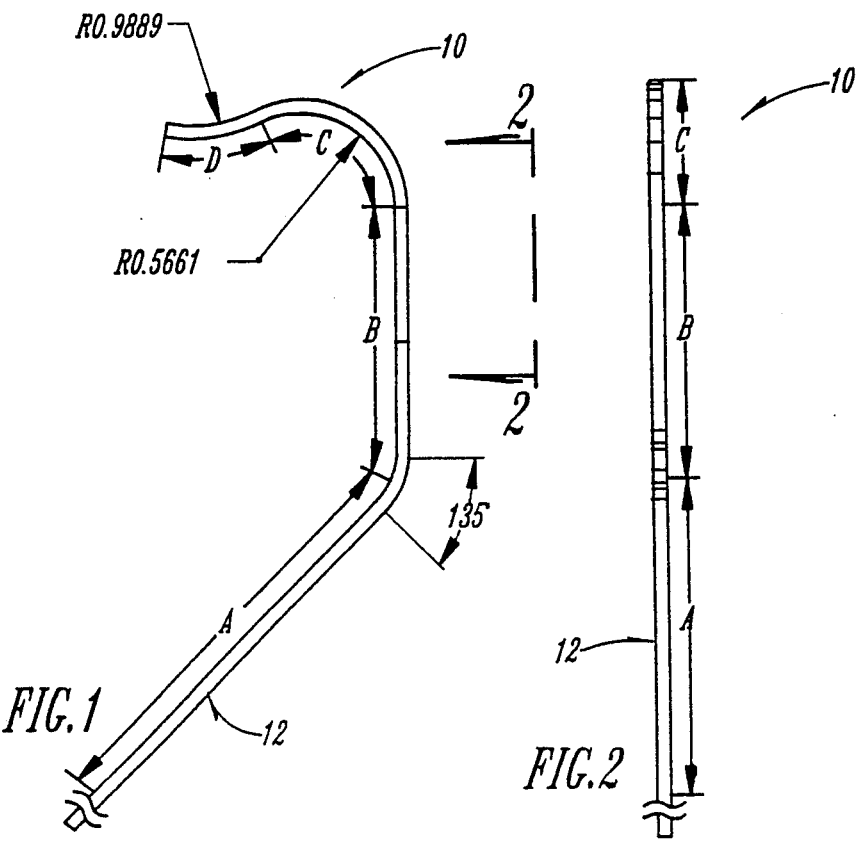
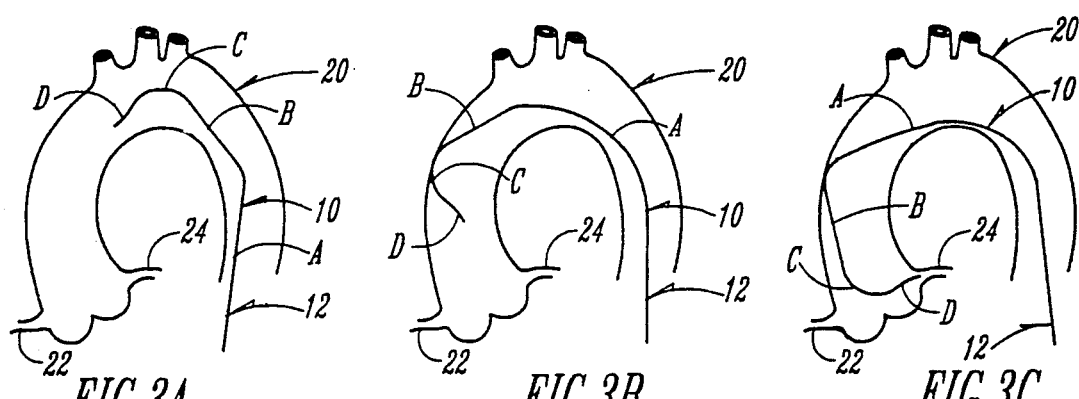
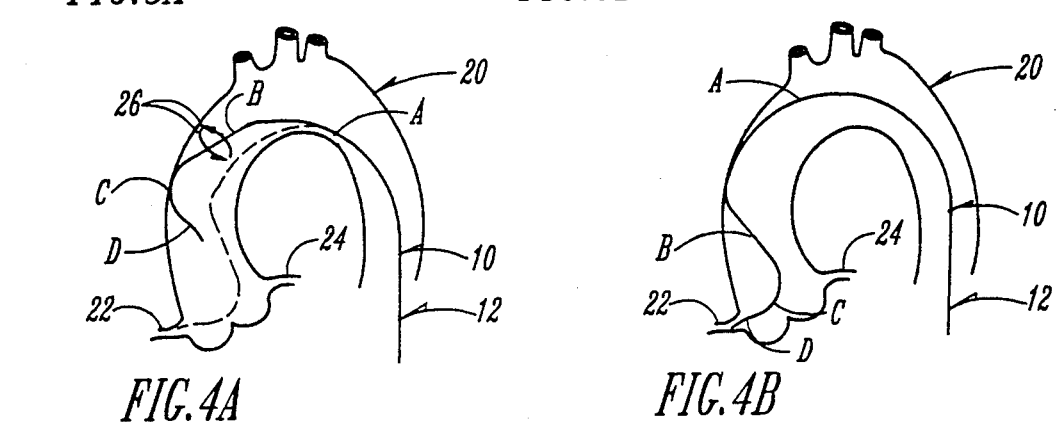

CARDIAC CATHETER

BACKGROUND OF THE INVENTION

A. Field of the Invention

The present invention relates to catheters, and in particular, to catheters utilized in investigative and therapeutic procedures with respect to the main coronary arteries of the heart.

B. Problems in the Art

The procedures involved with cardiac catheterization are well known in the art. Cardiac catheterization generally is used to investigate the condition of the main coronary arteries. The usual procedure is to utilize a long narrow flexible tubular catheter inserted into an artery either in the groin area or in the patient's arm. The catheter is moved up the artery and into the coronary arteries near the heart to inject x-ray dye (contrast media) into the coronary arteries to allow cardiologists to diagnose the existence or severity of coronary artery disease. Catheters can also be used as the conduits for guide wires for such things as dilatation balloons used in angioplasty. Other uses are possible.

The coronary arteries branch out from what is called the aortic arch. What are called ostia are the openings between the aortic arch and the left and right main coronary arteries. It is generally advantageous, and sometimes necessary, to be able to enter the ostia for these procedures.

One problem that exists with cardiac catheterization is that there are different sizes and shapes of aortic arches and different locations and distances between the aortic arch and the ostia for access to the coronary arteries. Therefore, the conventional solution in the art is to have available a number of differently sized and shaped catheters to allow the doctor to select essentially what is believed to be the best fit for a particular patient and organ configuration.

Different types of catheters are used or are preferred for different types of cardiac procedures. Furthermore, certain materials may be preferred for the catheters. Certain catheters are desired to be made of a more flexible material to allow more deformation, and therefore more flexibility as far as maneuvering and positioning the distal end of the catheter. On the other hand, more rigid, less flexible materials are desired by some to allow easier insertion through the long distance to the aortic arch. However, the less flexible materials are more difficult to conform to curves and bends, and run the risk of damage to the arteries or complications because of the nature of the material.

As can be appreciated, cardiac catheterization is not a trivial procedure. It requires the cardiologist to introduce the distal end of the catheter in an artery in the patient's limb (arm or leg) and then basically push the catheter up the artery to the aortic arch. Because of the limited ability to manipulate the tip once in the artery, the tip usually must have some sort of inherent configuration that would allow it to enter at least one coronary artery by simply pushing on the proximal but remotely located end. The inherent nature of the ostia into the coronary arteries is such that a straight ended catheter, while being fairly effective inserted through the limb arteries, does not function to effectively traverse the aortic arch and to enter the ostia.

No single catheter is known which allows easy and safe access to both ostia. Therefore, the state of the art is such that when investigation of one coronary artery is completed, the catheter has to be completely removed. A second catheter of a different shape is then inserted to investigate the second coronary artery. This is called catheter exchange. This greatly adds to the time, effort, and difficulty of these procedures, including risk associated with any such procedure.

It is therefore a principle object of the present invention to offer an improvement with respect to the problems, deficiencies, and needs in the art.

It is another object of the present invention to provide a cardiac catheter which can be used for both diagnostic and therapeutic cardiac procedures.

A further object of the present invention is to provide a cardiac catheter which can access both coronary ostia, including those with anatomically varied locations.

Another object of the present invention is to provide a cardiac catheter which may avoid the need for catheter exchange to access both ostia.

A still further object of the present invention is to provide a cardiac catheter which is stable in the sense that it can be inserted into a patient's limb artery and safely and efficiently moved to a location at or near the coronary ostia, and safely and effectively manipulated into the coronary ostia.

Another object of the present invention is to provide a catheter which is flexible enough to be manipulated as needed, and is safer than more inflexible designs.

These and other objects, features and advantages of the present invention will become more apparent with reference to the accompanying specification and claims.

SUMMARY OF THE INVENTION

The present invention includes a cardiac catheter of a generally defined shape and configuration to allow access to both coronary ostia for most patients. It will eliminate in most instances the requirement for catheter exchange for the purpose of access to both coronary ostia.

The catheter according to the present invention has a distal portion which generally is C-shaped in nature. Its most distal section is essentially perpendicular to an intermediate basically linear section. The distal-most section consists of a double curve or reverse curve.

The intermediate portion is in turn connected at an obtuse angle to a third portion which extends to the remainder of the catheter.

The catheter is made of a material which is somewhat flexible. The shape of the catheter, however, allows efficient and effective control and placement to conventional desired locations regarding catheterization procedures.

BRIEF DESCRIPTION OF DRAWINGS

FIG. 1 is a side plan view of the distal portion of a cardiac catheter according to a preferred embodiment of the present invention.

FIG. 2 is an edge view taken along line 2—2 of FIG. 1.

FIGS. 3A–3C illustrate diagrammatically the utilization of the catheter of FIG. 1 for access to the right coronary ostia of a patient.

FIGS. 4A and 4B illustrate diagrammatically the utilization of the invention of FIG. 1 for access to the left coronary ostia of a patient.

DETAILED DESCRIPTION OF THE PREFERRED EMBODIMENT

To assist in a better understanding of the invention, one preferred embodiment will now be described in detail. The description will refer to the drawings described above. Reference numbers and letters will be used to indicate specific parts and locations in the drawings. The same reference characters will indicate the same parts or locations in all the drawings, unless otherwise indicated.

Cardiac catheterization techniques have been described in numerous publications. See for example pages 174-180, CARDIAC CATHETERIZATION AND ANGIOGRAPHY, William Grossman. Such background information is incorporated by reference herein.

The preferred embodiment of the present invention is shown at FIG. 1. The cardiac catheter 10 includes what will be called a distal portion 12 which is shown in FIG. 1. The majority of the body of catheter 10 is not shown and can take on various configurations. It would generally be elongated (perhaps 110 centimeters in length) and fairly straight in nature.

Distal portion 12 has a unique shape. A proximal-most section A is essentially linear. What will be called intermediate section B is connected obtusely to section A and is also linear in nature. In the preferred embodiment the angle between sections A and B is 135 degrees. This is the most preferred relationship but can vary.

Sections C and D consist of what is called a reverse or double curve. Those combined sections extend generally perpendicular from the distal-most end of Section B. It is noted that distal end 12, in its entirety, is roughly C-shaped in the sense that it is in generally one plane (see FIG. 2) and forms roughly a three-sided shape, between its two ends.

In the preferred embodiment shown in FIG. 1, section C consists of an arc segment of a circle defined by a radius of 0.5661 inches. Section D is an arc segment of a circle described by a radius of 0.9889 inches. The radius of curvature of section C is therefore roughly half of that of section D.

Intermediate section B, in the preferred embodiment, is roughly 3.5 to 5 centimeters long. Section C is approximately 33 mm in length; whereas Section D is approximately 15 millimeters in length. FIGS. 1 and 2 therefore show the basic configuration of distal portion 12.

In the preferred embodiment, catheter 10 is made of the following material:

A vascularly compatible polymer plastic such as polyvinylchloride, or similar material, reinforced with a flat metallic or Kevlar braid, and coated in its inner lumen with a hydrophyllic and/or friction reducing material. This material is somewhat flexible and therefore is safer when inserting and manipulating through the arteries.

FIGS. 3A-C and 4A-B illustrate the use of catheter 10. Aortic arch is shown at reference numeral 20. The left and right ostia are shown at 22 and 24, and again represent the openings into the left and right main coronary arteries respectively. The aortic arch is basically C-shaped. Therefore, by correct positioning of distal portion 12 of catheter 10, its own C-shape will basically conform to that of the aortic arch 20. FIGS. 3A-B illustrate that the flexible nature of catheter 10 allows it to assume a basically straight shape while traveling into the aortic arch 20 (see FIG. 3A). Distal portion 12 then begins to revert to its original shape (FIG. 3B) as it traverses the apex of the aortic arch 20. Section C of distal portion 12 serves as a guide and assists in allowing distal portion 12 to conform to and traverse aortic arch 20. Finally, FIG. 3C illustrates how the reverse curve of Section D is then in a position to conform with the position and shape of the right ostium 24. Catheter 10 can then be inserted into the right ostium 24 simply by additional pushing of the proximal end of catheter 10.

To access the left ostium 22, FIG. 4A simply shows that catheter 10 can be withdrawn from the right ostium 24 by withdrawing catheter 10 a short distance; and then rotating catheter 10 as indicated, for example, by arrows 26 in FIG. 4A. This would rotate sections C and D approximately 180 degrees so that, as shown in FIG. 4B, by pushing forward with catheter 10 the distal end would be configured to self-guide itself into the left ostium 22. Again the curve of section C would assist in forming a guide to avoid snags or other complications when pushing forward on catheter 10.

Of course, either the left or right ostium could be accessed first in time or second in time. The benefit of distal portion 12 is the ability to access both without having to withdraw catheter 10 and insert a different catheter 10.

The included preferred embodiment is given by way of example only, and not by way of limitation to the invention, which is solely described by the claims. Variations obvious to one skilled in the art will be included within the invention defined by the claims.

For example, the material of the preferred embodiment of catheter 10 could be different than disclosed previously if it retains the similar characteristics. The exact angles, curves, and dimensions can vary within reasonable ranges.

What is claimed:

1. A catheter for accessing left or right ostia for cardiac catheterization procedures comprising:
    a generally C-shaped distal portion of the catheter having distal and proximal ends;
    the distal portion of the catheter including a first curved section beginning at the distal end of the distal portion, extending to a second curved section curved in an opposite direction to the first curved section, and terminating in an end;
    a first elongated generally straight portion, having a longitudinal axis and first and second opposite ends, extending from the end of the second curved section, the first and second curved sections extending generally perpendicularly from the first end of the first elongated generally straight portion; and
    a second elongated generally straight portion connected obtusely to the second end of the first elongated generally straight portion and extending to the proximal end of the distal portion of the catheter in generally the same plane as the first and second curved portions and on the same side of the longitudinal axis of the first elongated generally straight portion as the first and second curved portions.

2. The catheter of claim 1 wherein the first curved section has a radius of curvature.

3. The catheter of claim 2 wherein the radius of curvature is based on a radius of approximately one inch.

4. The catheter of claim 1 wherein the second curved section has a radius of curvature.

5. The catheter of claim 4 wherein the radius of curvature of the second curved section is based on a radius of approximately one-half inch.

6. The catheter of claim 1 wherein the first curved section has a radius of curvature which is greater than the second curved section.

7. The catheter of claim 1 wherein the second elongated generally straight portion is connected at approximately 135 degrees to the first elongated generally straight portion.

8. The catheter of claim 1 comprising a third elongated generally straight portion connected to the second elongated generally straight portion.

9. The catheter of claim 8 wherein the third elongated generally straight portion is longer in length than the first and second elongated generally straight portions.

10. The catheter of claim 1 wherein the distal portion is made of a flexible material.

11. The catheter of claim 1 comprising a further section of the catheter connected to the proximal section.

12. The catheter of claim 11 wherein the further section of the proximal section is elongated.

13. A catheter for cardiac procedures comprising:
an elongated catheter body having a proximal end and a distal end;
the catheter body consisting of three sections, a proximal section beginning with the proximal end, a distal section terminating in the distal end, and an intermediate section between the proximal and distal sections, all sections being aligned and generally in one plane;
the proximal section comprising a generally linear portion; the intermediate section comprising a generally linear portion connected obtusely to the proximal section; and
the distal section comprising a double curved portion in said plane and extending generally perpendicularly to the intermediate portion on the same side of the intermediate portion as the proximal section, and having a first segment curved in a first direction defined by a first radius and a second segment defined by a second radius and curved in an opposite direction.

14. The catheter of claim 13 wherein the obtuse connection of the intermediate section to the proximal section is approximately 135 degrees.

15. The catheter of claim 13 wherein the total length of the distal section is at or near the length of the intermediate section.

16. A method for cardiac catheterization comprising:
forming a generally planar, distal end of a flexible catheter into a substantially C-shaped member including a proximal straight section, a second section connected at approximately 135 degrees to the proximal section, and a third section comprising a double curve generally perpendicular to the second section, the double curve having a first portion with a radius of curvature that is less than the second portion which is curved in an opposite direction from the first portion;
sizing the distal end so that the proximal end of the proximal, second, and third sections approximate the shape of a typical aortic arch;
inserting the catheter into a primary limb artery of a patient whereby the flexible nature of the catheter allows the catheter to assume a generally linear shape;
pushing the catheter through the artery until it reaches the aortic arch;
rotating the catheter so that the curvature of the third section is aligned with the curvature of the aortic arch;
further pushing the catheter so that the distal portion travels around the aortic arch in order to position the end of the catheter generally adjacent an ostium;
further rotating the catheter depending on whether the left or right ostium is desired to be entered;
pushing the catheter to insert the end of the catheter into the selected ostium; and
performing the catheterization procedure through the catheter.

17. The method of claim 16 further comprising the steps of:
withdrawing the catheter end from the selected ostium;
rotating the catheter approximately 180 degrees along its axis while the catheter end is in the aortia arch; and
pushing the catheter to enter the other ostium.

18. The method of claim 16 wherein the catheter is used for the injection of dye into a coronary artery.

19. The method of claim 16 wherein the catheter is used for angioplasty procedures.

* * * * *